(12) United States Patent
Mueller et al.

(10) Patent No.: US 6,391,021 B1
(45) Date of Patent: *May 21, 2002

(54) METHOD FOR NON-SYNCHRONOUS LASER-ASSISTED MYOCARDIAL REVASCULARIZATION WITH STATIONARY FIRING

(75) Inventors: Richard L. Mueller, Byron; Michael J. Rosinko, San Jose, both of CA (US)

(73) Assignee: Eclipse Surgical Technologies, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/327,938

(22) Filed: Jun. 8, 1999

Related U.S. Application Data

(63) Continuation-in-part of application No. 08/904,222, filed on Jul. 31, 1997, now Pat. No. 5,931,834, which is a continuation-in-part of application No. 08/729,325, filed on Oct. 15, 1996, now Pat. No. 5,785,702.

(51) Int. Cl.[7] .............................................. A61B 18/24
(52) U.S. Cl. ............................... 606/7; 606/10; 606/15
(58) Field of Search ........................................ 606/3–19

(56) References Cited

U.S. PATENT DOCUMENTS

| | | | |
|---|---|---|---|
| 4,658,817 A | 4/1987 | Hardy | 128/303.1 |
| 4,784,132 A | 11/1988 | Fox et al. | 128/303.1 |
| 4,800,876 A | 1/1989 | Fox et al. | 128/303.1 |

(List continued on next page.)

FOREIGN PATENT DOCUMENTS

| | | |
|---|---|---|
| WO | WO 96/35469 A1 | 5/1996 |
| WO | WO 96/35469 | 11/1996 |
| WO | WO 98/31281 | 7/1998 |

OTHER PUBLICATIONS

Deckelbaum, Lawrence I., M.D., "Cardiovascular Applications of Laser Technology," Lasers in Surgery and Medicine 15:315–341, 1994.

Deckelbaum, "Cardiovascular Apps. of Laser Tech.", Lasers in Surgery and Medicine, 15:315–341 (1994).

*Primary Examiner*—David M. Shay
(74) *Attorney, Agent, or Firm*—Gibson, Dunn & Crutcher LLP

(57) ABSTRACT

A method of selecting laser parameters for performing laser-assisted myocardial revascularization to avoid inducing undesired cardiac arrhythmia without synchronization of delivery of laser energy and the patient's cardiac cycle, the method comprising the steps of minimizing the power level of laser energy used, thereby decreasing the overall trauma to the heart, selecting a pulse frequency as great as possible while avoiding adverse summation effects, selecting a pulse width as wide as possible to prevent excessively high peak powers per pulse and not so wide as to cause undesired thermal damage, selecting an energy flux rate, shaping the front end of each pulse of laser energy to provide efficient, non-explosive TMR channeling, and correcting the selected power level, pulse width, pulse frequency and energy flux rate for mechanical events, including method of access to the heart, position of selected portions of myocardium in the heart, temporal duration of the procedure, natural movement of the heart, specific heart geometry, pre-existing heart arrhythmia and other factors causing a predisposition to heart arrhythmia. A method for performing laser-assisted transmyocardial revascularization (TMR) and percutaneous transluminal myocardial revascularization (PTMR) using such laser energy with parameters selected to avoid inducing undesired cardiac arrhythmia, the method comprising the steps of generating laser energy having a predetermined non-square wave shape, a predetermined wavelength, a predetermined energy flux and a predetermined power level, and delivering the laser energy in a plurality of pulses, the plurality of pulses having a predetermined pulse frequency and a predetermined pulse width, to selected portions of myocardium to form TMR and PTMR channels without synchronizing delivery of the laser beam with the cardiac cycle.

38 Claims, 5 Drawing Sheets

U.S. PATENT DOCUMENTS

| | | |
|---|---|---|
| 4,848,336 A | 7/1989 | Fox et al. ................ 128/303.1 |
| B14,784,132 A | 3/1990 | Fox et al. ..................... 606/15 |
| 5,041,108 A | 8/1991 | Fox et al. ..................... 606/7 |
| 5,125,926 A | 6/1992 | Rudko et al. ................ 606/19 |
| 5,380,316 A | 1/1995 | Aita et al. ..................... 606/7 |
| 5,389,096 A | 2/1995 | Aita et al. ..................... 606/15 |
| 5,620,439 A * | 4/1997 | Abela et al. ............. 606/15 X |
| 5,672,170 A * | 9/1997 | Cho et al. ................ 606/11 X |
| 5,703,985 A | 12/1997 | Owyang |
| 5,785,702 A * | 7/1998 | Murphy-Chutorian et al. . 606/7 |
| 5,840,075 A * | 11/1998 | Mueller et al. ............... 606/11 |
| 5,876,373 A | 3/1999 | Giba et al. |
| 5,931,834 A | 8/1999 | Murphy-Chutorian |

* cited by examiner

METHOD FOR NON-SYNCHRONOUS LASER-ASSISTED MYOCARDIAL REVASCULARIZATION WITH STATIONARY FIRING

RELATED APPLICATIONS

This application is a continuation-in-part of U.S. patent application Serial No. 08/904,222 entitled METHOD FOR NON-SYNCHRONOUS LASER-ASSISTED TRANS-MYOCARDIAL REVASCULARIZATION filed Jul. 31, 1997, now U.S. Pat. No. 5,931,834 which is a continuation-in-part of U.S. Ser. No. 08/729,325 entitled METHOD FOR NON-SYNCHRONOUS LASER-ASSISTED TRANS-MYOCARDIAL REVASCULARIZATION, filed Oct. 15, 1996, issued Jul. 28, 1998 as U.S. Pat. No. 5,785,702, both of which are incorporated herein by reference.

FIELD OF THE INVENTION

The present invention relates to a procedure known as laser-assisted myocardial revascularization, and more particularly, to improved methods for revascularization of the heart by creating a plurality of small pathways or channels through predetermined portions of the heart using laser energy delivered via a laser delivery means according to specific parameters, including variable frequency, and without requiring synchronization of laser energy delivery with the beating of the heart.

BACKGROUND OF THE INVENTION

Much of the heart consists of a special type of muscle called myocardium. The myocardium requires a constant supply of oxygen and nutrients to allow it to contract and pump blood throughout the vasculature. One method of improving reduced myocardial blood supply is called trans myocardial revascularization (TMR), the creation of pathways or channels into the myocardium generally from either an outer epicardial surface of the heart in a surgical procedure or from an inner endothelium cell covered surface of a heart's endocardium chamber in a percutaneous transluminal myocardial revascularization (PTMR).

A procedure using needles in a form of myocardial acupuncture was used clinically in the 1960s. Deckelbaum. L.I., Cardiovascular Applications of Laser Technology, Lasers in Surgery and Medicine 15:315–341 (1994). The technique was said to relieve ischemia by allowing blood to pass from the ventricle through the channels either directly into other vessels perforated by the channels or into myocardial sinusoids which connect to the myocardial microcirculation. These sinusoidal communications vary in size and structure, but represent a network of direct arterial-luminal, arterial-arterial, arterial-venous, and venous-luminal connections. Interest in miyocardial acupuncture or boring, which mechanically displaces or removes tissue, decreased when it was discovered that the mechanically created channels closed because of acute thrombosis followed by organization and fibrosis of clots.

By contrast, recent histological evidence of patent, endothelium-lined tracts within pathways created with laser energy supports the assumption that the lumen of the laser pathways is or can become hemocompatible and resist occlusion caused by thrombo-activation and/or fibrosis. A thin zone of charring occurs on the periphery of the laser-created transmyocardial channels through the well-known thermal effects of optical radiation on cardiovascular tissue. This type of interface may inhibit the immediate activation of the intrinsic clotting, mechanisms because of the inherent hemocompatibility of carbon. In addition, the precise cutting, action that results from the high absorption and low scattering of laser energy ($CO_2$, Ho, etc.) may minimize structural damage to collateral tissue, thus limiting the tissue thromboplastin-mediated activation of extrinsic coagulation. Recent histological studies show that both patent and non-patent channels promote growth of an alternate circulation, one of the mechanisms believed to be beneficial following the procedure. Despite the creation of patent channels and pathways with lasers, there are reported problems associated with laser TMR procedures. Such problems can include channel closure which may be caused by selection and use of TMR laser parameters which do not produce channels with the characteristics detected in the histological evidence discussed above. An additional reported problem encountered in TMR procedures is adverse effects created by the laser on the diseased hearts of TMR patient's.

U.S. Pat. No. 4,658,817 issued Apr. 21, 1987 to Hardy teaches a method and apparatus for TMR using a surgical $CO_2$ laser including a handpiece for directing a laser beam to a desired location. Hardy suggests that the creation of TMR channels using a laser may affect contractility of the heart and states that the number of perforations may have to be limited accordingly.

Two subsequent patents, U.S. Pat. No. 5,380,316 issued Jan. 10, 1995 and U.S. Pat. No. 5,389,096 issued Feb. 14, 1995 both to Aita et al., discuss in general methods for intra-operative and percutaneous myocardial revascularization, respectively. Both patents suggest synchronization of the laser with the heart beat is necessary to avoid arrhythmias. PCT WO 96/35469 issued Nov. 14, 1996 to Aita et al. also discusses apparatus and general methods for percutaneous myocardial revascularization synchronized with the heart beat to avoid arrhythmias.

Synchronization of the laser energy delivery with the beating of the heart was also considered an important tool in U.S. Pat. No. 5,125,926 issued Jun. 30, 1992 to Rudko et al., reportedly to reduce the chance of laser induced fibrillation. Rudko et al teaches a heart-synchronized pulsed laser system for TMR. Utilizing electrical sensing, the heart beat is monitored using an EKG device. The device automatically delivers what appears to be a square pulse of laser energy to the heart only in response to electrical detection of a predetermined portion of the heartbeat cycle.

The prior art discussed above suggests that at least some pulsed laser systems and parameters are potentially damaging to the beating heart or its action and may induce fibrillation or arrhythmia, hence the need for heart synchronization to minimize such effects.

An arrhythmia is a disturbed heart rhythm which often takes over as the primary rhythm of the heart, as evidenced by a rapid flutter or other rhythm of the heart muscle, which renders it ineffective at pumping blood through the vasculature. The process of delivering laser energy to tissue results in polarization of individual cells of the heart in the area of delivery of the laser energy. Polarization of the specialized conducting cells as well as myocardial cells drives the action potential of cells resulting in responsive contractile motion. Delivering laser energy can disrupt the normal rhythm of the heartbeat since the cardiac rhythm can be side-tracked to that of the polarized cells as opposed to propagating through the heart along the normal path of the impulse.

The heart's natural, primary pacemaker is found in a group of cells called the sinoatrial or sinus node located near the junction of the superior vena cava and the right atrium.

The electrical impulse originates in the endocardium and propagates through the myocardium to the epicardial surface. The electrical impulse is conducted out of the sinus node to the atria, where it stimulates atrial muscle cells to contract, and to the atrioventricular node. Upon leaving the atrioventricular node, the electrical impulse continues to propagate down the conducting system to the bundle of His, into right and left branches thereof. The right bundle spreads the electrical impulse to the right ventricle and the left bundle branch propagates the impulse to anterior and posterior positions in the left ventricle to reach the Purkinje fibers. These small fibers form a rapid conduction network through the myocardium to deliver the impulse to all of the individual contractile muscle cells of the myocardium.

The electrical signal travels at different speeds at different parts of the network. While electrical signals on the portion of the network extending through the atria have been found to travel at velocities of about 1 meter per second, these signals slow to about 0.2 m/s as they pass through the atrioventricular node. Signal propagation through the ventricular Purkinje network, however, is much faster—approximately 4 m/s. Thus, the sinus node is responsible for producing a repeating electrical impulse which ultimately causes the muscle cells of the heart to contract in repetitive, wave-like convulsions.

The synchronization solutions proposed in the prior art discussed above do not address methods for detecting and compensating for hard to detect, abnormal conduction patterns or rhythms which may occur in damaged hearts. Additionally, EKG monitoring may not detect and allow compensation for localized or isolated areas of heart tissue which may not be synchronized with other areas of heart tissue. Excitation of such isolated areas may cause arrhythmias. In addition to the problems discussed above, heart synchronization as described in the prior art limits the amount of time the laser can be activated during a heart cycle, thereby increasing the time of a TMR procedure.

A need exists in the prior art for a method and apparatus for performing TMR and PTMR procedures quickly using specified laser parameters selected to minimize possible cardiac arthythmias without the need for monitoring the heart beat.

ADVANTAGES AND SUMMARY OF THE INVENTION

Thus, it is an advantage of the present invention to provide a method for performing both transmyocardial revascularization (TMR) and percutaneous transluminal myocardial revascularization (PTMR) with laser energy having parameters selected to avoid cardiac arrhythmia.

A method for TMR and PTMR with laser energy having parameters selected to avoid cardiac arrhythmia comprises the following steps, in combination of: determining a wavelength of the laser energy from a laser selected to perform either TMR or PTMR; using the wavelength determination to select parameters for the laser energy to produce a non-square wave shape; generating the laser energy at the determined wavelength with the selected parameters to produce the non-square wave shape; and delivering the generated laser energy in one or more pulses to selected portions of heart tissue to perform either TMR or PTMR in the myocardium without inducing cardiac arrhythmia and without synchronizing delivery of the laser energy to a cardiac cycle site. When using a Holmium:YAG laser in either a TMR or PTMR procedure, the selected parameters are power level, energy flux, pulse width, and pulse frequency. In a TMR or PTMR procedure, the laser energy has a wavelength of between about 1.8 and about 2.2 microns, an energy flux of between 0.7–1.78 $J/mm^2$ and a power level of at least about 3 watts, the laser energy being delivered with a pulse frequency of at least about 5 Hertz and a pulse width of between about 150 and about 350 microseconds, the laser energy as delivered causing about 0.5 millimeters or less lateral necrosis surrounding a TMR treatment. When using a Xe:Cl excimer laser in either a TMR or PTMR procedure, the laser energy has a wavelength of about 0.308 microns, a power level of between 0.3–2.0 watts and an energy flux of between about 25–80 $mJ/mm^2$, and is delivered with a pulse frequency of between about 5–25 Hz and a pulse width of between about 20–200 nanoseconds, and causes about 5 microns lateral necrosis surrounding the TMR channel produced thereby. When using a $CO_2$ laser for the TMR procedure, the laser energy has a wavelength of about 10.6 microns, an energy flux of about 51 $J/mm^2$ and a power level at least about 800 W, is delivered in a single pulse about of 0.05 seconds and can be gated, and causes between about 0.03 to about 0.2 millimeters lateral necrosis surrounding a TMR channel produced. When using an Argon laser for TMR, the laser energy has a wavelength of between about 0.488 and about 0.514 microns, an energy flux of about 1.3–12.74 $J/mm^2$ and a power level at least about 1–10 W, is delivered in a single pulse, and causes approximately 4 mm lateral necrosis surrounding a TMR channel produced thereby, and is generated by an Argon laser. When using a Nd:YAG laser in a TMR procedure, the laser energy has a wavelength of about 1.06 microns, an energy flux of about 9.5–13 $J/cm^2$ and a power level at least about 2–100 W, is delivered with a pulse frequency of about 1–10 Hz and a pulse width of about 10 nanoseconds, and causes at least about 15 mm lateral necrosis surrounding a TMR channel produced thereby. When using an Er:YAG laser for the TMR procedure, the laser energy has a wavelength of about 2.94 microns, an energy flux of about 50–500 $J/mm^2$, is delivered with a pulse frequency of about 1–15 Hertz and a pulse width of about 1–250 microseconds, and causes about 0.1 millimeters lateral necrosis surrounding a TMR channel produced by an Er:YAG laser.

In a preferred embodiment, the laser energy is delivered to the selected portions of heart tissue using a catheter apparatus with laser delivery means, the method further comprising the following steps of introducing the catheter apparatus with laser delivery means percutaneously into the vasculature of the patient; and positioning the laser delivery means at the endocardial surface of the selected portions of heart tissue. In a preferred embodiment, the laser energy is delivered to the selected portions of heart tissue in a procedure using laser delivery means where the revasculature site is accessed by positioning the laser delivery means at an endocardial surface of the heart tissue through inside a patient's coronary artery. In a preferred embodiment, the method further includes the step of mechanically piercing the endocardial and/or myocardial layer heart tissue prior to delivering the laser energy into the myocardium thereby creating a welling affect by the surrounding endocardial tissue. In a preferred embodiment, the method further includes mechanically piercing the endocardial surface adjacent the selected portions of heart tissue prior to delivering the laser energy into the myocardium and penetrating no more than half the wall thickness of the myocardium.

The TMR method comprises the following steps of generating laser energy having a non-square wave shape, a selected wavelength, a selected energy flux and a selected power level; and delivering the laser energy in a plurality of pulses, the plurality of pulses having a selected pulse frequency and a selected pulse width, to selected portions of myocardium without cardiac arrhythmia and without synchronizing delivery of the laser beam with the cardiac cycle. In a preferred embodiment, a variable number of pulses of laser energy is delivered with a variable pulse frequency between 5–20 Hz. In a preferred embodiment, the laser energy is delivered with a variable pulse repetition rate of between about 1 and 10 pulses. In a preferred embodiment, the laser energy is delivered with a constant pulse frequency of between about 5 and 20 Hertz and a variable pulse preset limit of between about 1–10 pulses. In a preferred embodiment, the laser energy is delivered in a pulsed mode at a high repetition rate of fixed frequency, the method using a laser with an optical shutter and in which the shutter of the laser is opened and closed in response to a random sequence of commands. In a preferred embodiment, the pulsed laser energy is delivered in a pulsed mode pulsed at a high repetition rate of fixed frequency, the method using a laser with a controllable flashlamp and in which the flashlamp is allowed to fire only during certain pulses within the fixed frequency laser operation in response to a random sequence of commands. In a preferred embodiment, the laser energy is delivered in a pulsed mode pulsed at a random, variable frequency rate.

It is a further advantage of the present invention to provide a method of selecting laser parameters for performing laser-assisted TMR or PTMR procedure to avoid cardiac arrhythmia and without synchronization of delivery of laser energy to a patients s cardiac cycle. The method comprises the following steps, in combination: selecting a minimum power level of laser energy to be used, the minimum power level being sufficient to ablate heart tissue; setting a pulse frequency as great as possible and selected to avoid summation effects; setting a pulse width as long as possible and selected to prevent excessively high peak power without causing undesired levels of thermal damage during TMR or PTMR; shaping a front end of each pulse of laser energy to provide non-linear pulses to avoid cardiac arrhythmia during TMR; and correcting the selected power level, pulse width, pulse frequency, pulse width, and shaping for mechanical events. In a preferred embodiment, the selected parameters are a single pulse, power level, energy flux, and pulse width. Numerous other advantages and features of the present invention will become readily apparent from the following detailed description of the invention and the embodiments thereof, from the claims and from the accompanying drawings in which the details of the invention are fully and completely disclosed as a part of this specification.

DETAILED DESCRIPTION OF PREFERRED EMBODIMENTS

Figure 1A:
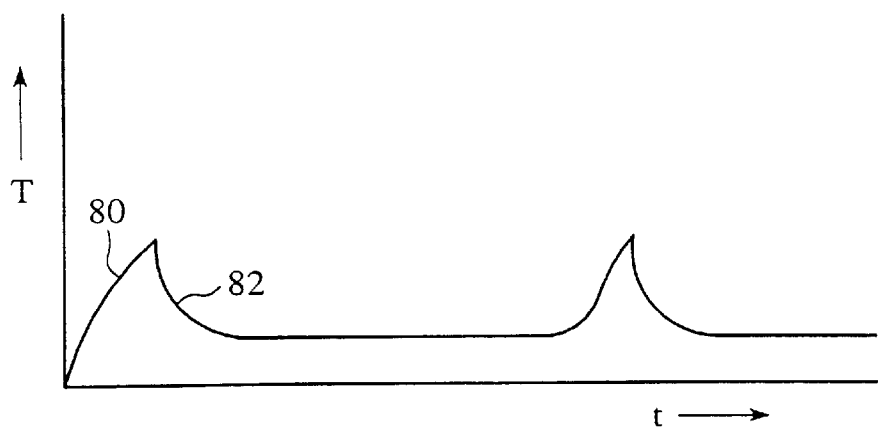
FIGS. 1A–1C are graphical representations of the process of summation.

This invention teaches laser parameters which, in optimized combinations, reduce or eliminate the risk of inducing arrhythmia while performing a laser-assisted TMR and PTMR. The methods described herein do not require cardiac monitoring or any other form of synchronization of laser delivery with the natural cardiac rhythm. The present invention is intended for use with any medical laser. In particular, excimer and Holmium lasers, including many of various different types known and available now or at any time, are particularly suited to the present invention. However, any suitable laser source, pulsed or otherwise, may be used to provide laser energy to the laser delivery means of the present invention for performing the method of the present invention. Other laser sources include but are not limited to $CO_2$, argon, neodymium: yttrium aluminum garnet (Nd:YAG) as well as erbium: yttrium aluminum garnet (Er:YAG). The following laser operating parameters have been determined to be optimal parameters for performing laser-assisted revascularization without causing arrhythmias.

| | | | | Laser Operating Parameters | | |
|---|---|---|---|---|---|---|
| Type | Xe: Cl excimer | Ho: YAG | $CO_2$ | Argon | Nd: YAG | Er: YAG |
| Wavelength | 0.308 μm | 2.1 μm | 10.6 μm | 0.488–514 μm | 1.06 μm | 2.94 μm |
| Laser Pulse Frequency | 5–25 Hz | Greater than Approx. 5 Hz pulsed | Single pulse, CW or super-gated | CW- multimode, can be q-switched or | 1–10 Hz; CW or pulsed; CW can be "gated" | 1–15 Hz |
| Energy Flux | About 25–80 mJ/mm² | About 0.7–1.78 J/mm² | About 51 J/mm² | About. 1.3–12.75 J/mm² | About. 9.5–13 J/cm² pulsed; About. 8–27 J/mm² CW | About 50–500 J/mm² |
| Laser Pulse Width | About 20–200 ns | About 150–350 ps | About 0.05 s | N/A | 10 ns, CW or pulsed | About 1–250 μs |
| Wave Shape | Non-square | Non-square | Non-square | N/A | Non-square | |
| Ave. Power | 0.3–2.0 W | Greater than 3 W | 800 W | 1–10 W | 2–100 W | |

-continued

| Laser Operating Parameters | | | | | | |
|---|---|---|---|---|---|---|
| Type | Xe: Cl excimer | Ho: YAG | $CO_2$ | Argon | Nd: YAG | Er: YAG |
| Lateral Necrosis | About 5 $\mu$m | About 0.5 mm | About 0.05–0.2 mm 10–15 $\mu$m | Greater than about 4 mm q-switched | Greater than about 15 mm mm | About .025–0.1 |

The above laser operating parameters for various types of lasers were selected to enable laser energy to smoothly and gradually interact with the tissue of the heart thereby avoiding, where possible, sharp and sudden tissue interaction. A contoured, smooth, gradual application of energy will provide less shock to the heart itself. A non-square wave with a relatively shorter pulse width generally is preferred to achieve such smooth and gradual tissue interaction. It will be recognized by those skilled in the art that achieving the desire effect requires variation of the individual elements of the laser operating parameters depending upon the type of laser selected. Each laser operating parameter is discussed separately below.

Wavelength

It is recognized that numerous medical lasers having different wavelengths are currently available. Selection of an appropriate wavelength depends at least in part upon the tissue to be treated with the laser. For TMR, the mechanism of delivering laser energy to the water component of heart tissue to effect ablation and channeling highly efficient. Mid-infrared lasers, such as the 2.1 micron wavelength Holmium:YAG laser, are well suited for cutting and ablating heart tissue because, in general, wavelengths longer than approximately 1.4 microns are highly absorbed by water. It is by means of this strong absorption in water that mid-infrared laser energy is converted to heat energy in tissue.

If the energy density in the tissue is high enough, the tissue vaporizes. Since water is the primary constituent of most soft tissue, about 80% or more, the correlation is fairly accurate, although there will be minor differences between absorption of mid-infrared energy in water and in tissue, as well as between different types of tissue. The mid-infrared absorption spectrum of water is well known and absorption coefficients over a larger range are available.

The absorption coefficient of the 2.1 micron Holmium:YAG laser is about 26 $cm^{-1}$. This modality is highly efficacious for cutting and ablating. For comparison, the absorption coefficients of the 1.06 micron wavelength energy created by the Neodymium:YAG laser and the 10.6 micron radiation produced by a $CO_2$ laser are 0.13 and 823 $cm^{-1}$, respectively. The inverse of the absorption coefficient is directly correlated with energy absorption depth d:

$$d=1/\alpha$$

A large absorption coefficient implies a short penetration depth. Penetration is short because the energy is immediately absorbed by the cells closest to the source and does not extend into the tissue.

Other lasers include the Xe:Cl excimer laser which delivers energy at 0.308 $\mu$m, the argon laser which delivers energy at between about 0.488–0.514 $\mu$m, the $CO_2$ laser which delivers energy at 10.6 $\mu$m, and the Nd:YAG laser which delivers energy at 1.06 $\mu$m.

$CO_2$ lasers used in a fluid environment in near-contact procedures, despite a relatively short penetration depth, have the disadvantage in that even a thin film of water between the fiber and the tissue will greatly diminish the effective laser power because of the large absorption coefficient. Hence, the use of gas insufflation is generally required with the $CO_2$ laser. Furthermore, $CO_2$ lasers generally require further manipulation of parameters to create TMR channels.

In selecting a particular wavelength for a laser, and adjusting parameters to compensate for differences in absorption by the tissue, it is important to consider the need to achieve an end result of a non-square wave.

Pulse Width and Frequency

To prevent electrical arrhythmia of the heart during TMR or PTMR, it has been found that certain pulse widths not only assure minimal and predictable thermal damage to surrounding tissue but are less likely to interfere with the cardiac signal which may lead to arrhythmia. By reducing the interval between pulses to significantly shorter than the interval of a beating heart at approximately 60 beats per minute, or 1 beat per second (1 hertz), there is much less chance that a single laser pulse will side track the electrical rhythm and take over propagation of the electrical impulse throughout the heart. Furthermore, higher frequencies create a hole faster thereby reducing the probability that a laser polarized group of cells in the area of channel creation will short circuit a heartbeat signal. In a preferred embodiment of the method of the present invention, pulse widths less than about 300 microseconds, and preferably lower than about 200 microseconds, have been found to be most effective. Thus, in a preferred embodiment of the method of the present invention, frequency rates greater than 5 hertz and preferably between about 5 hertz and about 25 hertz are least likely to induce electrical arrhythmia during TMR.

The Holmium:YAG or other comparable pulsed laser can be pulsed at a certain rate or within a range of rates. Pulsed application of laser energy to effect vaporization and ablation of the tissue has been demonstrated to be preferable in some instances to application of laser energy in a single pulse. In delivering energy to tissue, a given volume of tissue will absorb laser energy converting it into heat. To ablate a given target volume of tissue it is necessary to put enough heat energy into the volume to vaporize it. A certain minimum rate of delivery of energy is required to counteract the effect of thermal relaxation which is the phenomenon by which heat diffuses out of the heated volume of tissue. The thermal relaxation time $\tau$ is defined as the amount of time required for a given amount of heat to diffuse out of a given volume of tissue. Based upon an estimation that the thermal diffusivity of tissue is very close to that of water, and using classical heat transfer theory, the thermal relaxation time period for a spot size of tissue using a 400 micron diameter fiber in contact or very close proximity to the tissue has been calculated to be between approximately 57 and 286 milliseconds using the following equation:

$$1/\tau = 4\alpha^2 K + 16K/d^2$$

where K=thermal diffusivity of tissue, d=diameter of the illuminated spot. The calculation is based on the estimate that K–1.4×10$^{-3}$ cm$^{-2}$/s.

In general, the pulse width must be optimized to prevent a peak power spike while achieving a predetermined energy flux for ablation or any other procedure. Too short a duration will require too sharp an energy spike with a very high peak power level. On the other hand, too long a pulse will result in summation of energy effects which result in overheating, an increased zone of thermal necrosis, and possible other coagulation type effects.

It will be understood that the Nd:YAG, Ho:YAG, Xe:Cl excimer and Er:YAG lasers are all pulsed lasers in at least preferred forms, and therefore optimum pulse widths may be selected. Appropriate pulsing will avoid summation effects and will provide a contoured, gentle leading edge of the energy delivery profile.

Use of a continuous wave laser, such as argon, some Nd:YAG and some $CO_2$ lasers, typically can be enhanced by mechanically chopping the continuous wave to reduce unfavorable thermal effects. The advantage to chopping such laser beams is to reduce or eliminate adverse summation effects on the tissue. However, mechanically chopping a continuous wave does make it more difficult to achieve a non-square or otherwise less assaultive delivery of laser energy. In any event, as discussed below, whether delivering pulsed energy or continuous wave energy, the rate at which it is delivered is also important. Too narrow of a pulse width at too low of a power level will fail to create patent channels. Thus, the power of the laser beam, or the amount of energy delivered to the tissue in terms of Joules per second, is also an important factor to consider.

In general, optimal pulse frequencies and pulse widths to avoid arrhythmias combine to create a relatively narrow pulse width delivered at a relatively high pulse frequency.

Energy Flux and Power

Energy flux $E_{pulse}$ or fluence, also referred to as radiant exposure or energy density, is expressed in units of pulse energy per area, or joules per square centimeter. The threshold radiant exposure $F_{th}$ is defined as the single pulse threshold for the ablation of biologic tissue. For radiant exposures less than this threshold, tissue is not vaporized or ablated, but, instead, is heated. For radiant exposures higher than this threshold, tissue is vaporized. Thus, for effective ablation, the energy per pulse divided by the area of the spot size must be greater than the threshold radiant exposure.

$$E_{pulse}/A > F_{th}$$

As an approximation, the threshold energy per unit volume for water is known to be 2500 joules per cubic centimeter. This is also the heat of vaporization, or the heat required to raise one cubic centimeter from about body temperature to steam at 100 degrees centigrade. This threshold energy per unit volume is given by the equations:

$$F_{th} \times \alpha \text{ or } F_{th}/d$$

Depth of penetration, discussed above, is equal to the inverse of the absorption coefficient and the threshold radiant exposure for biologic tissue is about 100 joules per square centimeter. An effective energy flux must be at least this great. Experimentally, threshold energy flux rates of between about 5 and 75 joules per square centimeter are found.

The average power $P_{av}$ of a repetitively pulsed laser is equal to the energy per pulse times the number of pulses per unit time ($P_{av}$=joules/pulse×pulses/second, in watts). The number of tissue parcels ablated per second is equal to the repetition rate of the laser in pulses per second, or hertz. Thus, increasing the pulse repetition rate to increase the average power delivered to the tissue linearly increases the rate of tissue removal.

If a region of tissue is illuminated by more than one pulse, an excess of energy accumulates in the tissue. For example, if the individual pulse energy and spot size provide an energy flux below the single pulse threshold radiant exposure $F_{th}$, but the interval between pulses at a particular repetition rate is shorter than the characteristic thermal relaxation time τ, a parcel or given volume of tissue may be ablated after a number of pulses has impinged the tissue. This process is referred to as summation.

Figure 1B:
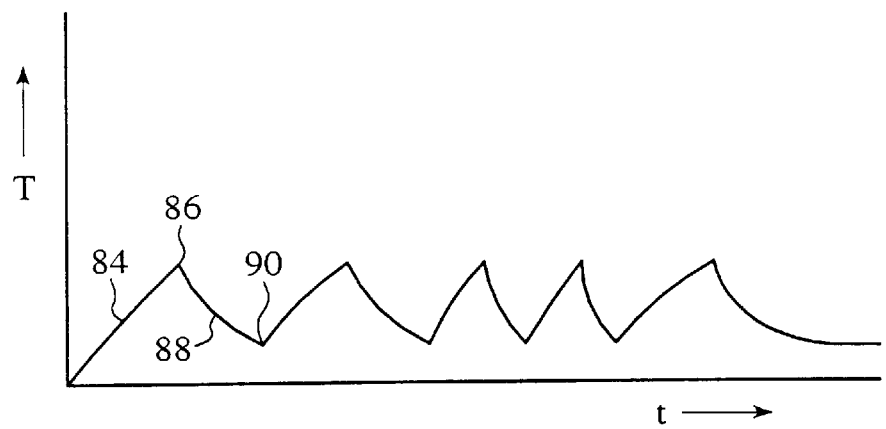
Figure 1C:
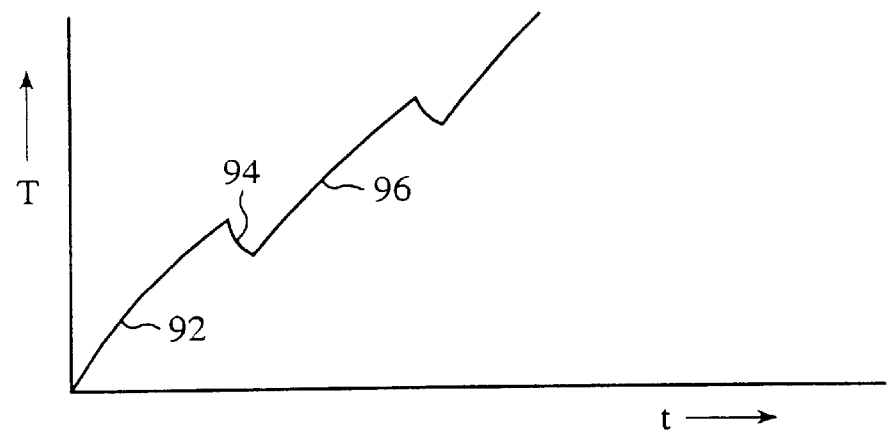

FIGS. 1A–1C are graphical representations of the process of summation. In FIG. 1A, an initial pulse of energy 80 increases the temperature (T) of the tissue locally. However, given a large amount of time (t) between pulses, the temperature of the tissue drops rapidly and immediately at 82 during the beginning of the delay period (D) following irradiation with no net result. Referring now to FIG. 1B, decreasing the time between pulses results in a positive net result and tissue ablation. An initial pulse of energy 84 increases the local temperature to a certain point 86, and then the temperature begins to drop during the time period 88 immediately following the first irradiation step. At an intermediate temperature level 90, another pulse of laser energy is delivered to impinge upon the tissue. The additional pulse elevates the temperature from temperature level 90 to a temperature 91 which is high enough to cause ablation. Repeated cycling as in FIG. 1B is very effective at achieving ablation without causing excess thermal damage in the surrounding tissue. During this mode of operation, the system can be described with the following equation:

$$(P_{av}/A)-(F_{th}/\tau)>0$$

(It should be noted that $F_{th}$ may not remain constant in this regime: only the first pulse encounters fully hydrated, native tissue at body temperature.) Effectively, this criterion indicates that ablation can generally take place only if energy is supplied faster than it diffuses away. Because the thermal relaxation time τ is between 57 and 286 milliseconds, the interval between pulses can be as short as between 20 and 50 milliseconds, which is shorter than the shortest thermal relaxation time that arises from laser interaction with biologic tissue. A repetition rate greater than 3.5 hertz will permit entry into this FIG. 1B regime, however, as described above, pulse frequencies of between 5 and 15 hertz are optimum for laser-assisted TMR in which the risk of electrical arrhythmia is optimally reduced. Using these parameters, an average power delivery will be greater than 6 watts, or 6 joules per second.

By further decreasing the period between laser pulses, an excess of heat builds up in the tissue as shown in FIG. 1C. After an initial temperature rise 92 and a brief period of thermal diffusion 94, a further pulse of energy 96 will continue to drive the temperature of the tissue upwards. Not only is this an inefficient modality for revascularization, but the risk of thermal runaway and associated thermal damage to surrounding tissue is very great. Additionally, an elevated temperature and excessive tissue damage will both tend to increase the risk of arrhythmia. Not only are the cells which are elevated in temperature more easily depolarized, as they lie in a period of relative refractivity, but thermal damage to cells also interferes with their normal firing and propagation of the electrical impulse.

Therefore, in general, the power of the laser used, or the rate of delivery of energy to the tissue, can be tailored to avoid collateral damage of subsequent pulses. Though summation and overheating are more of a problem with continuous wave lasers, too small a pulse width with too high a peak-power pulse with lasers such as the Xe:Cl excimer, though at relatively similar powers as other pulsed lasers, may also have a harmful, explosive result.

In summary, depending upon the laser selected, the energy flux and power parameters should be adjusted to ensure ablation without deleterious summation effects. The net result of such optimization is a reduction in the incidence of arrhythmia during TMR or other laser procedure.

Wave Shape

As has been stated, adjustment of the parameters discussed above is designed to create a non-square wave for TMR and other laser applications. There is a direct correlation between likelihood of arrhythmia and wave shape. When TMR is performed using a wave with a square shape, that is, a wave which immediately and linearly increases to a near-maximum level, continues at that level until dropping sharply back to the lower level. A non-square wave would be one that is non-linear and had a more gradual increase in amplitude, or curve with a relatively lower slope, with a subsequent gradual decrease. Past experiences with square wave lasers in PTMR and TMR applications clearly demonstrate that the square waveform is more explosive and traumatic to the heart. A comparable energy wave with a Gaussian, bell-shaped or other shaped waveform does not have a tendency to create arrhythmias whereas square waveforms have a greater tendency to induce arrhythmia due to a resulting shock wave which adversely impacts the entire heart.

Figure 2A:
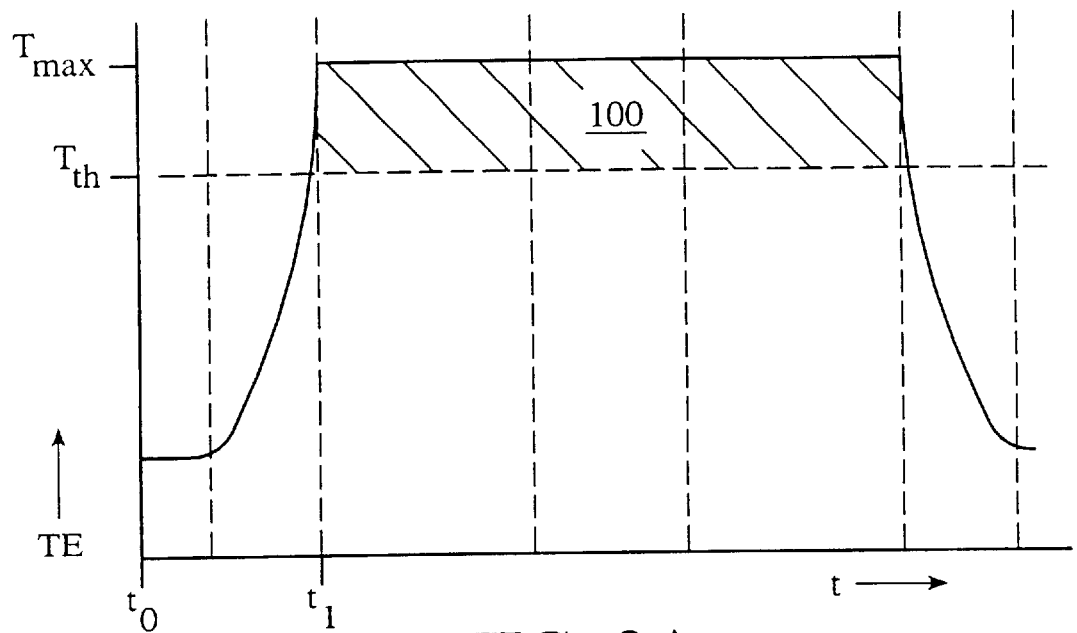
FIGS. 2A and 2B are graphical comparisons of the resultant difference between ablation with a square wave versus ablation with a non-square wave.
Figure 2B:
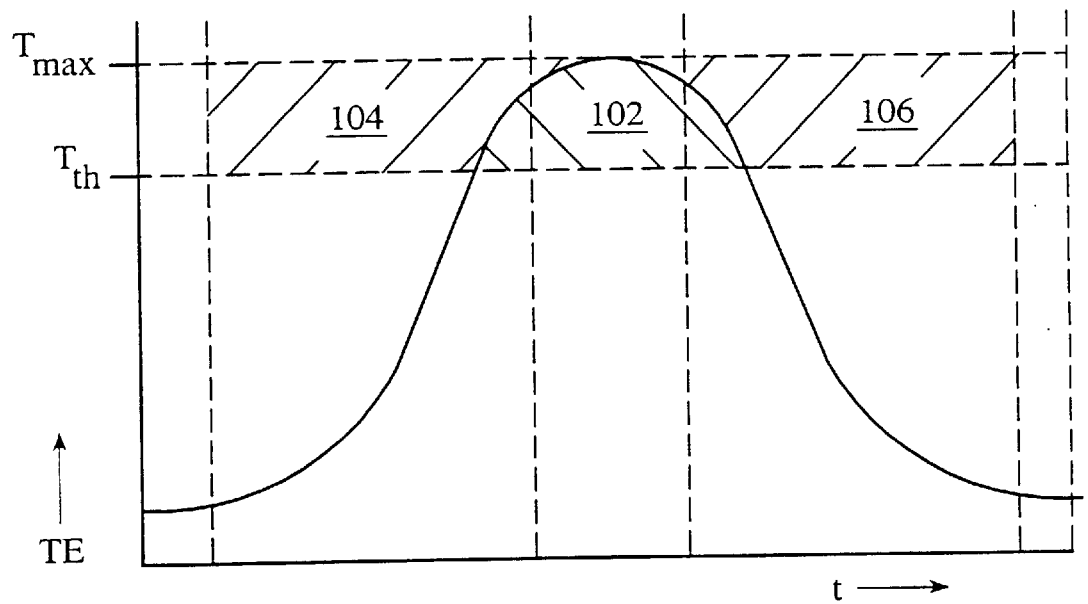

FIGS. 2A and 2B are graphical comparisons of the resultant difference between ablation with a square wave versus ablation with a non-square wave. In both plots, the vertical axis corresponds to both the temperature of individual cells in the volume of tissue heated by a single pulse as well as the energy level of those individual cells. In FIG. 2A, when a square-wave pulse is applied to the tissue, the temperature of the tissue rises sharply during the period between $t_0$ and $t_1$. As the population density of individual cells heated above the threshold temperature $T_{th}$ up to a maximum temperature $T_{max}$ is relatively large, the chance that one individual cell might depolarize and take over or capture the rhythm of the heart is increased. These cells at risk of taking over the heart rate and causing an arrhythmia are identified by the shaded portion of the graph 100. A large population of cells rapidly depolarize and any one can serve as a situs of arrhythmic activity. When the pulse of laser energy is non-square shaped as in FIG. 2B, the statistical probability that a single cell in the population of cells between $T_{th}$ and $T_{max}$ might capture the electrical cycle and become arrhythmic is much less. Assuming that a threshold temperature $T_{th}$ exists above which temperature individual cells may become depolarized (but below which the risk is very small), the area 102 under the non-square, generally bell-shaped curve in FIG. 2B is much smaller than area 100. It will be understood that the shaded areas under the curves above the threshold temperature levels generally are proportional to the probability that arrhythmia will be produced—the smaller the area the less likelihood of inducing an arrhythmic cardiac cycle. Thus, the areas 104 and 106 can be said to be proportional in magnitude to the decrease in likelihood that an errant depolarized cell will capture the cardiac cycle and cause arrhythmia.

The net effect of providing a non-square shaped pulse wave is to cause the same amount of ablation, perhaps over a slightly longer period of time, with a decreased risk of inducing arrhythmia. Bell or Gaussian-shaped waveforms have are highly effective at channeling in the TMR procedure and the risk of inducing arrhythmia is optimally minimized.

It is demonstrated that a non-square, contoured wave shape will tend to reduce the risk of causing arrhythmia in TMR and PTMR patient's. This is generally difficult to achieve with continuous wave lasers since chopping of a CW laser beam will not avoid a square or otherwise fairly sharp wave front. However, using pulsed lasers, optimization of a contoured wave will further eliminate a high peak-power spike at or near the center of the pulse. Such optimization will include adjustment of the other above parameters.

Zone of Lateral Necrosis

While the precise influence of thermal injury on TMR channel patency, or other desirable TMR result, is unclear, the extent of lateral thermal necrosis should be controlled by careful selection of the laser and its operating parameters. In general, minimizing lateral tissue necrosis will result in more efficient tissue removal from the channel itself, and will also result in minimal trauma to surrounding tissue. Although lateral tissue damage may be sought in some applications, in general, minimal trauma to surrounding tissues is a desirable goal.

$CO_2$ lasers have been found to produce an intense inflammatory response which may be inconsistent with provision and promotion of an alternative circulation, one of the therapeutic mechanisms believed to be associated with TMR. Although mechanically-formed channels were completely occluded within 2 days of formation by cellular infiltrate, eventually forming scar tissue, many laser created channels remain patent for a longer period of time, but too may become occluded with fibroblasts, macrophages and subsequently collagen.

Thermal injury to myocardium surrounding channels may delay healing and thus increase duration of patency, though the lack of an obvious, visibly patent channel may not preclude blood flow in vivo via the channels. However, it has been shown that it is possible to alter the degree of thermal injury, for example with the Ho:YAG laser, by changing pulse energy or repetition rate. It has also been shown that with laser created channels, the extent of tissue damage associated with the creation of the channels can be reflected in the degree of fibrosis produced. Fibrosis associated with the initial injury results in disorganization of adjacent myocytes. The observed disarray is similar to that found in viable muscle adjacent to a healed infarct. Hence the degree of muscle disorganization may be determined by the amount of channel-associated fibrosis.

The above described structural changes due to lateral thermal necrosis result in diminished heart function and also provide a substrate for abnormal electrical conduction. This may increase the chance of inducing arrhythmia during such procedure. An increase in interstitial collagen can be expected to affect heart function by decreasing contractility, elasticity and pumping strength, and can also be expected to decrease cell-to-cell contact.

Thus, in general, at least a minimum degree of thermal necrosis will be present and is considered beneficial. An excess of lateral necrosis, however, should be avoided since too great an amount of thermal injury will cause other complications non-beneficial to the TMR patient.

Miscellaneous Parameters

Another cause of tissue damage is the production of vapor bubbles in the tissue being ablated with lasers. The degree of myocardial disruption by such acoustic injury is slight at repetition rates of between about 2 and 3 Hertz, but vapor bubble effect may increase tissue injury in excess of that caused by temperature increases.

An additional consideration will be the temperature of the heart itself. In TMR procedures, cooling the heart will help prevent an accumulation of undesirable, potentially harmful heat. In other words, summation effects can be minimized by applying external cooling to the heart itself, or portions thereof, selectively or over large areas or otherwise, to effectively increase, by as much as several fold or more, the thermal relaxation time for the tissue.

Figure 3:
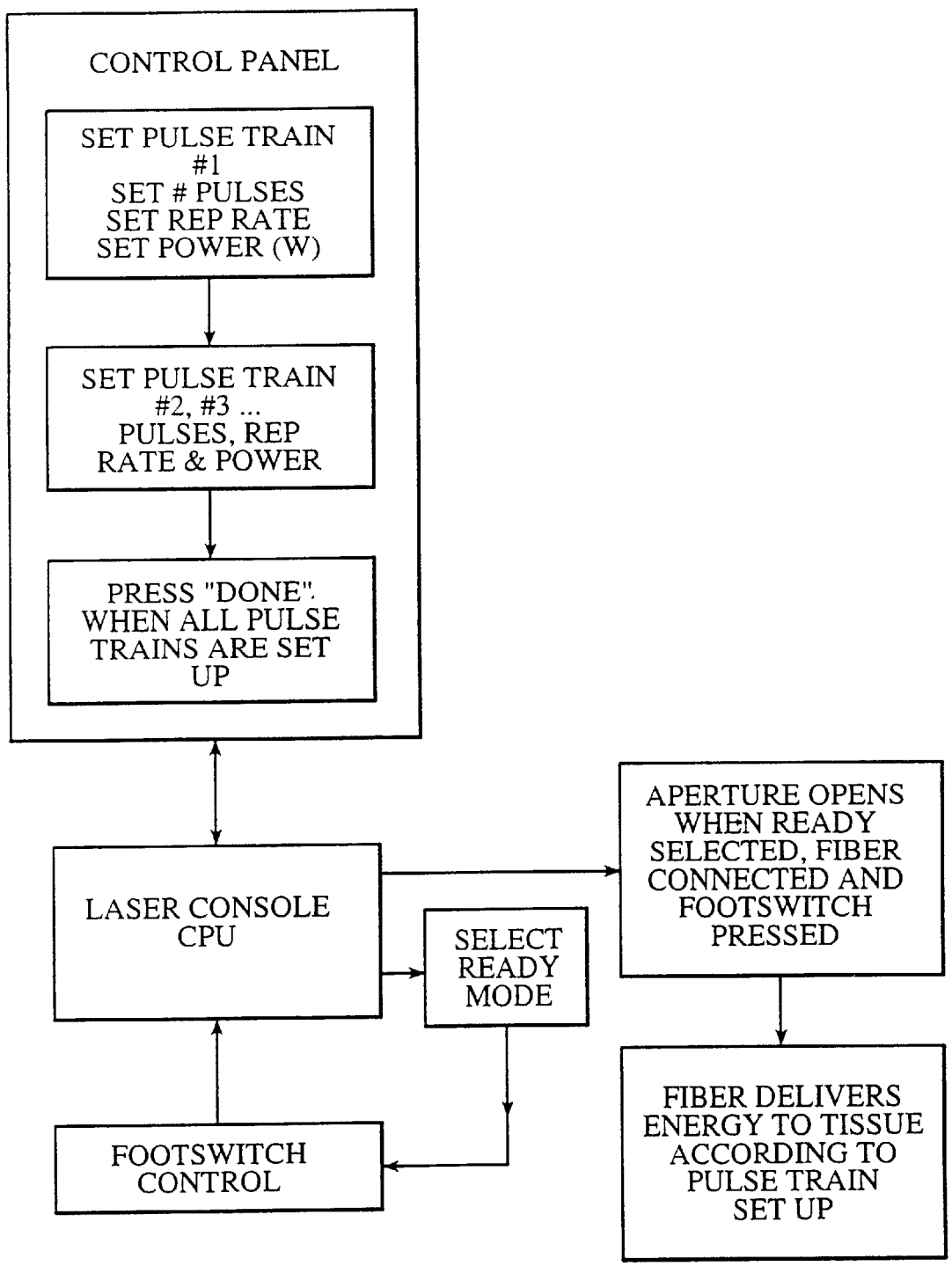
FIG. 3 is a flow chart demonstrating a method of selecting and setting variable laser parameters.

Variable Parameters The above discussion demonstrates various parameters for different laser energies chosen to minimize the possibility of arrhythmias and is based upon a generally constant, regular delivery of laser energy using those parameters. Arrhythmias also may be prevented by providing variable, or non-synchronous, delivery of laser energy. Non-synchronous TMR and PTMR procedures lessen the chance of capture of the heartbeat because the either of these procedures do not use a predictable, constant firing sequence for the heart to follow. FIG. 3 is a block diagram of a preferred embodiment of a method for non-synchronous laser-assisted TMR using variable parameters. Providing variable laser parameters further decreases the risk that surrounding tissue will abandon the regular pattern of the heart beat to follow the particular laser parameters used in the laser TMR procedure. The following table illustrates several variable laser parameters in TMR procedures with decreased risks of arrhythmias.

Variable Parameters

| MODE PULSE TRAIN | VARIABLE NUMBER OF RANDOMLY CHANGING PULSES | CONSTANT NUMBER OF PULSES DELIVERED/ VARIABLE PULSE REPETITION RATE | FIXED PULSE REPETITION RATE, PULSES GATED RANDOMLY |
|---|---|---|---|
| PULSE TRAIN #1 | 2 pulses 5 hertz 7 watts | 2 pulses 5 hertz 7 watts | 2 pulses 15 hertz 7 watts |
| PULSE TRAIN #2 | 3 pulses 15 hertz 7 watts | 2 pulses 10 hertz 7 watts | 3 pulses 15 hertz 0 watts = OFF |
| PULSE TRAIN #3 | 1 pulse 8 hertz 7 watts | 2 pulses 15 hertz 7 watts | 3 pulses 15 hertz 7 watts |
| PULSE TRAIN #4 | 2 pulses 6 hertz 7 watts | 2 pulses 8 hertz 7 watts | 1 pulses 15 hertz 0 watts = OFF |
| PULSE TRAIN #5 | | | 6 pulses 15 hertz 7 watts |

The variable parameters may be preset at the laser console control panel. As shown, the laser energy applied to the heart muscle in a TMR procedure is varied by providing (1) a variable number of pulses at a randomly changing pulse repetition rate, (2) a constant number of pulses delivered at variable pulse repetition rates, or (3) randomly gated pulse delivery at a fixed repetition rate. Mechanical or direct modulation may be used to vary the gating. Mechanical modulation is preferred using a mechanical device such as an automatic shutter or beam chopper.

Figure 4:
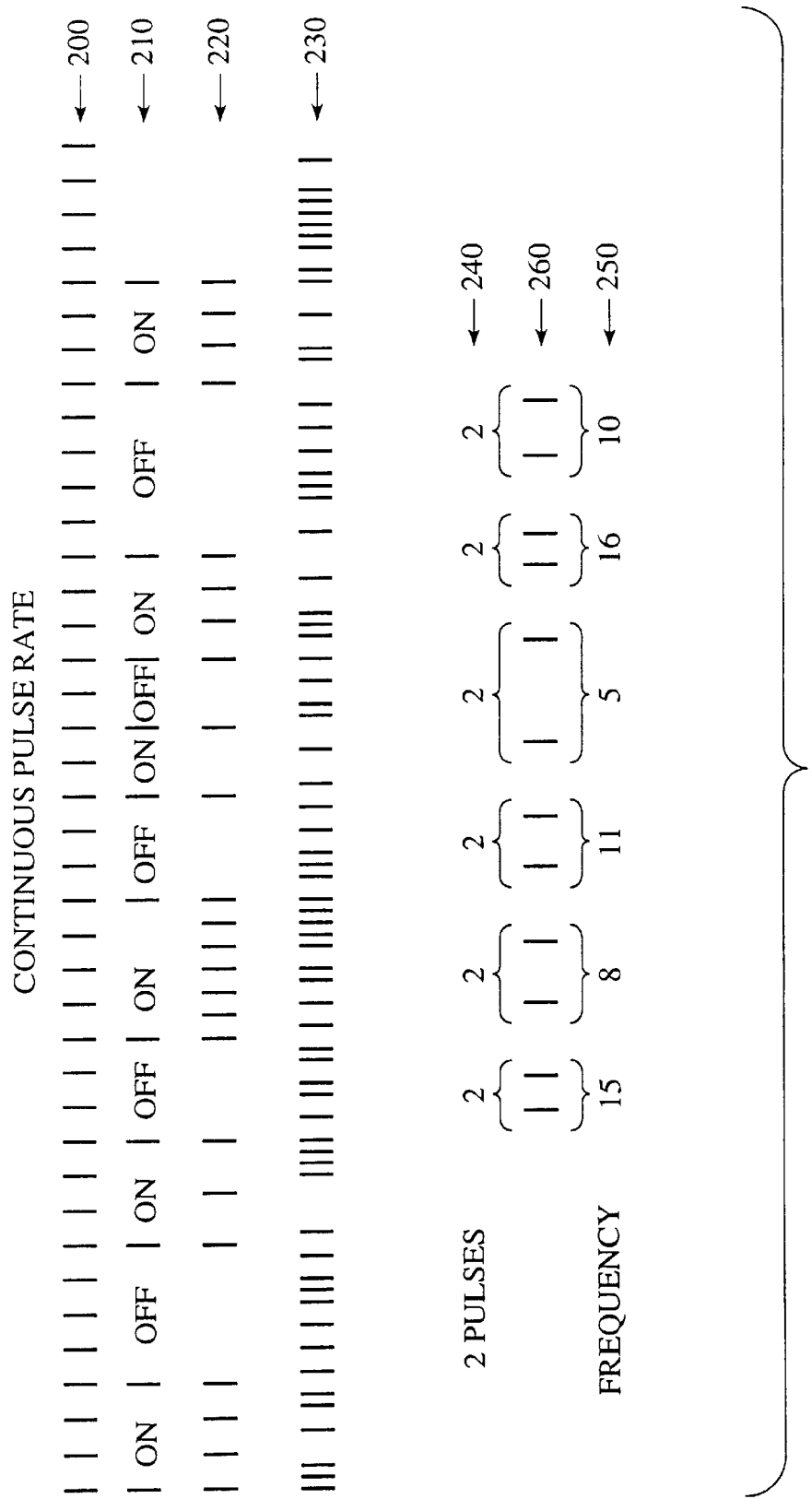
FIG. 4 is a representative example of variable laser parameters.

FIG. 4 is a representation of beam patterns which are possible using the variable laser parameter method of the present invention. One method of creating a random frequency of pulses is to provide an intra-cavity beam shutter. The laser is pulsed at a high repetition rate of fixed interval, for example 15–20 hertz. The system's central processing unit (CPU) or computer contains a pre-programmed random sequence of commands to open the shutter for a random period of time, and close the shutter for a random period of time until the foot switch is released. Thus, line 200 represents the fixed interval pulse rate of the laser. This is a constant rate, for example 15–20 hertz. Line 210 represents the controller's shutter operation. It is seen that the actual laser output during this time will be controlled in an on and off manner automatically by the operating program of the system CPU or other processor. Line 220 is representative of the actual output of the laser, allowing pulses of laser energy to be emitted during the on periods and suspending laser emission past the shutter during the off periods.

A second novel method for producing a variable laser output pattern is to control the flash-lamp of the laser as opposed to a mechanical shutter. As with the mechanical intra-cavity shutter, the laser is pulsed at a fixed repetition rate of, typically, 15–20 hertz. The system's CPU contains a pre-programmed randomized sequence of commands to allow the flash-lamp driver to fire only during certain pulses with the fixed repetition rate. A pattern similar to that shown in line 220 is possible in this manner.

A third method for producing a variable laser output is to control the flash-lamp directly. Instead of maintaining a continuous fixed repetition rate, of which only certain pulses are allowed to occur, this method uses a pre-programmed memory of variable repetition rates between about 5 and 20 hertz continuously delivered to tissue until the foot switch is released. This resultant beam pattern is depicted in line 230, a random pattern.

Yet a fourth method for producing a variable laser output is to change the repetition rate after a predetermined set number of pulses have been delivered. For example, the pattern shown in line 240 is a set of 2 individual pulses per each pulse repetition rate used. The random variation of repetition rate changes after each 2 pulse set, as shown in line 250 where the number of pulses per second is shown. The resultant beam pattern is depicted in line 260, a random pattern.

Percutaneous Transluminal Myocardial Revascularizaiotn (PTMR)

Selection of laser parameters for percutaneous transluminal myocardial revascularization (PTMR) procedures requires consideration of a number of difficulties encountered in most percutaneous ventricle procedures and consideration of factors particularly associated with PTMR. U.S. Pat. No. 5,389,096 issued Feb. 14, 1995, as discussed above and PCT WO 96/35469 published Nov. 14, 1996 to Aita et al., both discuss apparatus and general methods for percutaneous myocardial revascularization synchronized with the heart beat to avoid arrhythmias. Like Aita's U.S. Pat. No. 5,380,316 entitled "Method for Intra-Operative Myocardial Device Revascularization" which proposed that surgical TMR should be performed by lasing through the epicardium, these teachings suggest that conventional channels should be formed in a percutaneous procedure by firing laser energy from the endocardial surface, thereby destroying viable endocardial tissue. The percutaneous teachings briefly suggest in general terms that channels should extend into the myocardium at depths up to 10 mm. In particular, the '096 patent preferably suggests that channels are 1.5–2.0 mm in diameter with 10–30 mm depths from the endocardium into the myocardium. Both references are drawn particularly to methods and apparatus which attempt to stabilize the optical fiber device within the ventricle, and although both references note the obvious need to avoid perforation of the epicardium, neither reference addresses a number of problems particular to formation of laser revascularization channels in a PTMR setting.

Access to the ventricle for PTMR procedures is discussed in U.S. patent application Ser. No. 08/833,352 entitled Steerable Catheter, by Giba et al. filed Apr. 3, 1997, now U.S. Pat. No. 5,876,373, issued Mar. 2, 1999 which is hereby incorporated by reference. This application teaches of a percutaneous steerable laser delivery catheter that is positionable near the heart's endocardium for PTMR treatment. Pulsed laser energy that avoids cardiac arrhythmia is delivered to sections of heart tissue through an optical fiber disposed within the catheter. The catheter is inserted through the femoral artery in the groin region and passes into the inner heart over the aortic arch into the left ventricle. Channel formation in a PTMR procedure requires a catheter of lengths up to 120 cm which poses a number of problems which must be solved by a cardiologist controlling the channel forming device from a remote position outside of the body. In particular, many dynamic forces occur during optical fiber advancement through a catheter's lumen for correct positioning thereof in relation to the endocardial wall.

These forces include frictional forces within the catheter's lumen as well as forces encountered because of the patient's cardiac activity. For example, these variable forces are caused by 1) the overall length of the catheter and the attendant frictional forces caused by optical fiber advancement within the catheter 2) movement of the heart wall as the heart beats; and 3) variable tissue resistance to the optical fiber advancement through the spongy variable density endocardium with subsequent advancement through the denser myocardium. The endocardium, a porous variable density tissue layer, moves towards and away from a positioned catheter delivery system tip as the heart contracts and expands. This motion is resisted by the resilient nature of the catheter tip which attempts to bias the tip against the endocardial wall. The dynamic encounter between the endocardium and the distal tip of the catheter also poses potentially undesirable heart arrythmias due to mechanical forces created by optical fiber placement against the endocardium and subsequent advancement through the endocardial layer into the myocardium. During a PTMR procedure, the cardiologist must monitor these cumulative variable forces occurring at the catheter tip and perform laser tissue ablations using the catheter's proximal hand piece for both positioning the optical fiber tip and advancing the optical fiber as channel formation occurs.

PTMR channels must be created in tissue which, in addition to having variable densities, may vary in depth. The average thickness of the endocardium is approximately one mm or less and the thickness of the myocardium typically is approximately several cms or less. However, coronary anatomical irregularities may result in sections of the myocardium which are less than 10 mm in thickness. Unintended tissue ablations in thin areas of the myocardium may cause perforations through the epicardial wall leading to cardiac tamponade. Failure to account for differences in tissue density also may cause irregular channel formation with unwanted lateral necrosis. Laser parameters should be selected to take into consideration the relative ease in penetrating and advancing through the less dense endocardium as opposed to the relatively more difficult penetration and advancement into the denser myocardium. Laser power level(s) and/or pulse rate(s) must be correct to ensure proper fiber advancement to avoid irregular channel formation with unwanted lateral necrosis. Most important, procedural steps must be observed to select proper laser power level(s) and/or pulse rate(s) to ensure a patient's safety and well being.

Generally, PTMR laser parameters should be adjusted to compensate for several possible fiber optic delivery system positions, i.e. 1) juxtaposed or resting lightly against the endocardium without urging, 2) urged against the endocardium, and 3) pierced into the endocardium and juxtaposed to the myocardium. This is particularly true with smaller fiber optic delivery systems. In particular fibers smaller than 1 mm in diameter, piercing can be performed readily through the endocardium with the forces described. Any one of these three scenarios can occur while the heart is beating thereby causing variable density of the endocardium and myocardium. If the position of the optical fiber optic delivery system is not known or cannot be determined with certainty, prior to delivery of laser energy, laser parameters should be selected to ensure no harm would occur given any possible position of the fiber optic delivery system. For instance, delivering relatively high powered laser energy in scenario one without fiber advancement may cause cratering and destruction of the viable endocardium layer, or delivering such energy in scenario three with significant fiber advancement may cause perforation of the epicardium. Thus, the encountered catheter forces and uncertainties as to positioning the optical fiber tip in relationship to variable tissue densities bear upon the nature and quality of PTMR channel formation. Recent clinical studies have shown that PTMR procedures using laser parameters selected to form shallower channels will alleviate angina, create channels without significant damage to the endocardium or cratering, and incur minimal risk to a patient.

PTMR laser parameters are selected to provide a generally low power approach using a limited number of pulses for confined myocardium penetration to provide a safe mode to perform PTMR. Percutaneous laser revascularization procedures at lower power levels with limited number of pulses per channel formed relieve a patient's angina symptoms while ensuring optimal patient safety. These studies used a non-synchronous based PTMR system using a Holmium:YAG laser source, e.g. an Eclipse Surgical Technologies TMR-2000 with a laser catheter delivery system whose internal optical fiber was one mm in diameter. The catheter has a mechanism for advancing the fiber for short penetrations up to 5 mm depending upon left ventricle wall location. The patients who underwent this treatment experienced good results when a Holmium:YAG laser was operated at 5 Hz, in a preset pulse firing mode of up to five pulses/cycle, having an output average power of 3–4 watts where the laser pulse widths were between 100 and 250 ms, and the number of pulses per formed channel was less than five. Parametrically, the average power density/pulse in a pulse preset mode is approximately 1–4.5 watts/mm$^2$, the energy density is approximately 0.9 joules/mm$^2$, given an optical fiber diameter that varies between 600 and 1100 microns respectively. Patients experienced relief from severe angina when myocardium penetration was less than 3 mm. Lower average power at the 3–4 watt range per pulse with 1 mm diameter optical fiber and fiber advancement up to 5 mm compensated for many variables discussed above.

At a 3.5 watt setting operating at 5 Hz, the laser readily ablates approximately 1 mm sponge-like endocardial wall thickness and an additional 0.5 mm of denser myocardial wall thickness during the initial pulse, depending on tip location, with each subsequent pulse ablating approximately 0.5 mm of myocardium tissue. This step provides a welling action in the endocardial layer that assists in oxygenated blood transportation into the channels formed in the myocardium. Partial myocardial wall penetration for an average patient requires three or four pulses to achieve a 2–3 mm channel into the myocardium. For patients with greater predetermined left ventricle wall thickness, the fiber advance can penetrate up to 5 mm with five laser pulses being fired. The amount of energy delivered using 3–4 watts and a maximum of five pulses is insufficient to cause unwanted lateral necrosis or epicardium penetration in any of the three possible catheter tip delivery positions discussed above, but is sufficient to relieve angina. For example with optical fiber advancement limited to 5 mm, when an optical fiber tip is juxtaposed to the endocardium with a 3.5 watt setting where 3–5 pulses are fired, the laser pulses typically would form a channel approximately 2.5 to 3.5 mm depending upon whether the optical fiber is stationary or advancing after each pulse firing. If the fiber's optical tip pierces the endocardium prior to initial pulse firing and the laser is at the same power level and a pulse preset firing mode of 3–5 pulses, depth of the channel is approximately 3.5 to 4.5 mm depending upon whether the optical fiber is stationary or advancing after each pulse firing. Thus, the lower power settings provides a safety margin that ensures patient's safety in a worst case scenario.

Figure 5:
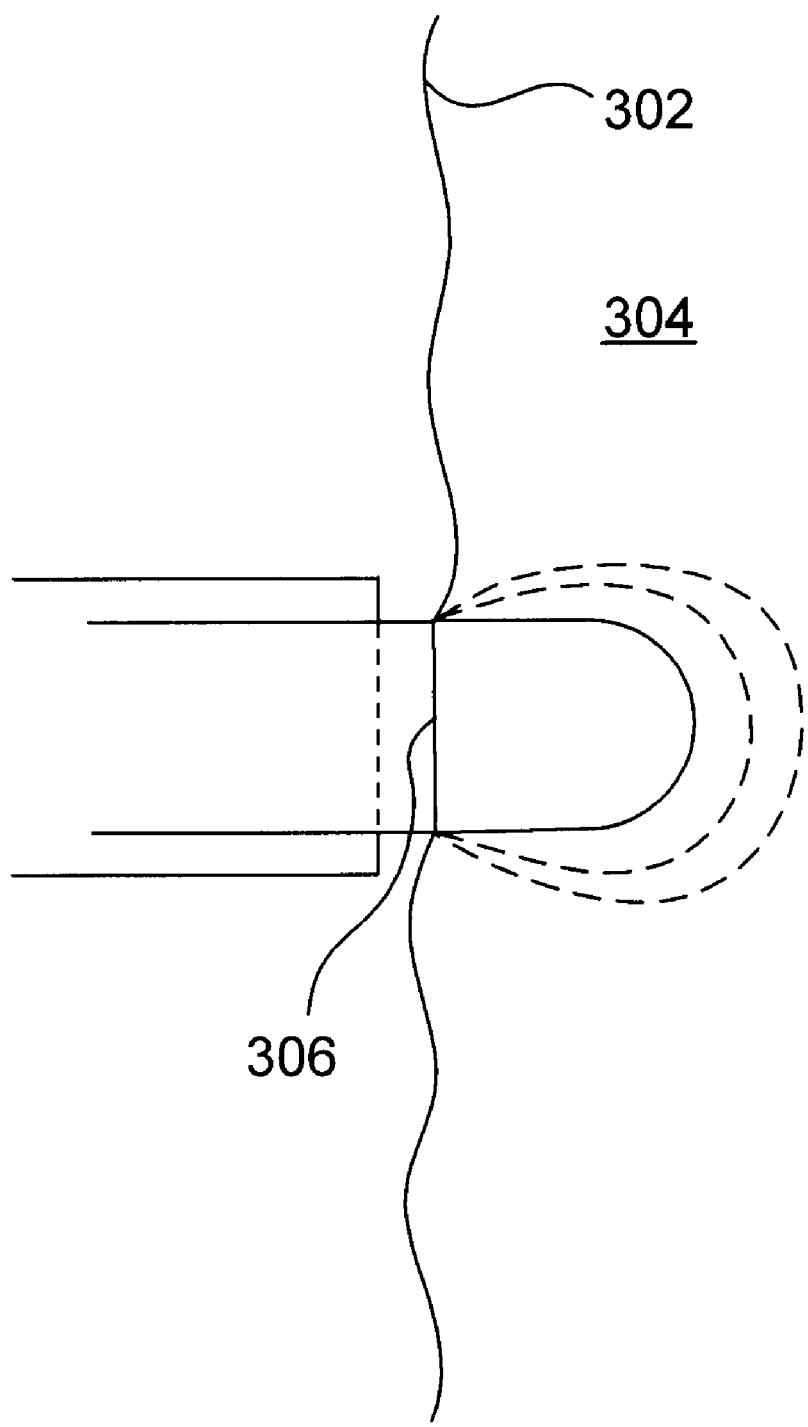
FIG. 5 is a representation of a stationary laser energy delivery device firing multiple pulses with increasing energy levels.

Allowing the optical fiber tip 306 to remain stationary, as shown in FIG. 5, for firing 2 to 5 pulses, preferably 3 pulses, wherein the energy level increases with each pulse, is advantageous in that it reduces the need of the operator or physician performing the myocardial revascularization procedure to coordinate firing and advancement of the laser delivery device and thereby allows for a greater control of channel depth. The increase in energy level may be a fixed percentage increase over the previous energy level, or the percentage increase may vary per pulse. Whether fixed or variable, the percent of increase would be in the range of about 15 percent to about 75 percent, with preferably a fixed increase in power per pulse of about 40 percent. Alternatively, the increase in energy level may be a fixed or variable joule increase per pulse in the range of about 0.1 joules to about 0.5 joules, preferably with a fixed increase in energy per pulse of about 0.3 joules. For example, an initial pulse energy level of 0.7 joule, followed by two pulses of 1.0 and 1.3 joules, respectively. A representation of the effect of firing a fixed or stationery fiber with multiple increasing energy levels is shown in FIG. 5. Any pulsed laser could be used with this embodiment, preferably a Holmium:YAG laser. Moreover, this embodiment is not limited to a PTMR procedure and is adaptable to TMR, wherein the range of pulse firing would be from about 7 to about 20 pulses. The fiber may be fired from a position against a surface of the heart 302, endocardium or epicardium, or from within the myocardium 304, particularly when the surface of the heart is mechanically pierced prior to firing.

Although low power in the 3–4 watt range is preferred, alternate parameters can be a single laser pulse with laser average power settings in a 7 to 9 watt range when the heart is contracted. Generally, the alternate parameter is particularly suitable when the delivery system is urged against endocardium, and the energy is delivered without fiber advancement. The single pulse prevents cratering and the energy perforates approximately no more than 5 mm, or half the typical thickness of the myocardium.

If a Xe:Cl excimer laser is used as the laser source in the PTMR procedure, the excimer laser operates at around a 50 mJ/mm² active fluence energy setting at 15 Hz. The laser ablates approximately 0.5 mm of the sponge-like endocardial wall thickness during initial pulsation at the inner endocardial wall where subsequent pulses in the myocardium ablate slightly less than 0.5 mm of myocardial tissue, these factors are dependent upon the heart's state and position of the fiber prior to pulsing. A channel in the myocardial wall for an average patient requires 8–10 pulses. For patient's with greater left ventricle wall thickness, the fiber advance can penetrate up to 5 mm using up to ten laser pulses.

If desired, the position of the catheter tip may be positively determined by partial or total piercing of the endocardial wall prior to delivery of a first laser pulse. A small diameter, i.e. less than 1 mm, or a piercing tip type optical fiber on a larger diameter fiber can be used as taught in U.S. patent application Ser. No. 08/638,677 entitled Optical Fiber Device for Laser Surgery Procedures, now U.S. Pat. No. 5,703,985 issued Dec. 30, 1997 and which is incorporated herein by reference. Piercing provides additional stability of the catheter tip to avoid destruction of endocardial tissue during a PTMR procedure and allow welling action to occur for oxygenated blood transport to the myocardial layer. The pulses penetrate the myocardium with an optical fiber advancement rate of approximately 0.5 mm after each laser pulse so as to create nearly uniform channels of cylindrical shape with minimal lateral necrosis. Differing heart anatomies may require up to five pulses. PTMR channels of approximately the same depth in the myocardium are created when delivering a single higher power laser pulse when the heart is in a systolic state and heart tissue density is greatest.

The cardiologist may observe the PTMR procedure on an imaging screen, e.g. using well known fluoroscopic procedures to observe the catheter's positioning in relationship to the endocardial wall. Also, an ultrasound imaging or ranging device in conjunction with the PTMR catheter as taught in U.S. patent application Ser. No. 08/852,977, and continuation-in-part U.S. patent application Ser. No. 09/169,747, entitled Ultrasound Device For Axial Ranging, which are hereby incorporated by reference, may be used to determine catheter tip position, particularly in the preferred low power embodiment when the fiber is advanced during delivery of the 3–5 pulses. The ultrasound device would ideally be used intermittently or in real time so that fiber advancement could be assured concurrent with each pulse.

Fiber advancement for the laser delivery device can typically be up to 5 mm. Compensation for greater depths of controlled penetration can be accomplished by adjusting either power and/or the number of pulses/formed channel. Any of the parameters discussed above may be easily controlled using the laser pulse preset mode which ensures that only the desired number of pulses are delivered upon activation of the laser delivery mechanism, typically a foot pedal with automatic laser shut-off even with continued foot pedal activation to ensure safety and controllability during either TMR and PTMR.

Method for Selecting Optimum Parameters

Based on the foregoing, a preferred method for determining the optimum parameters for performing TMR utilizing any suitable medical laser available will be apparent. At the outset, an initial consideration is to achieve the minimum threshold for tissue ablation and minimize the total amount of energy utilized to complete the procedure. Adapting parameters to this consideration will decrease the overall trauma to the heart and minimize the risk of inducing arrhythmia. A power setting which eliminates potential linear effects such as short, explosively high peak power pulses will be more desirable.

Additionally, when using a pulsed laser, which is in general more desirable than a continuous wave laser, increasing the pulse width, to prevent an excessively high peak power, to deliver a predetermined amount of energy in a given pulse, up to the point of thermal damage caused by summation effects, is desirable. In other words, the thermal relaxation time and factors which might affect that value including, but not limited to, heart temperature, is considered.

Furthermore, contouring or shaping the front end of the wave form to provide an efficient cutting or ablation wave shape but to prevent explosive, linear square wave shapes. Again, avoiding an excessively high peak power spike within the pulse will be advantageous.

Finally, correcting for mechanical events inherent in the selected TMR system, including but not limited to the elected access to the heart, duration of the entire procedure, manipulation of the laser delivery means and movement of the beating heart; and, mechanical events inherent in the individual patient, including but not limited to heart geometry, pre-existing heart arrhythmia or other factors causing a predisposition to such.

The present invention is intended for use with any medical laser. In particular, the Holmium or excimer laser is particularly suited to the present invention. However, any suitable laser source, pulsed or otherwise, could provide laser energy to the laser delivery means of the present invention for performing the method of the present invention. Likewise, the catheter and surgical equipment, including laser delivery means, referred to in the present document as well as that known and used in medicine and other disciplines today and in the future, will be included in the scope of this disclosure. Such laser delivery means include, but are not limited to, individual optical fibers as well as bundles of fibers, rods, mirrors configurations and other laser delivery means with and without focusing lens and the like. It will also be understood that the apparatus and method of the present invention as described herein, including the novel combinations or use with any conventional mechanism or method which are known to those skilled in the art, are included within the scope of this invention.

It will further be understood that while the present invention has been described for performing TMR on endocardial surfaces in the left ventricle, the apparatus and methods described herein are equally intended for use in any suitable procedure, including but not limited to procedures where any device need be extended through a guiding catheter to an opening or other point within the body for other medical procedures including laser treatment, visualization, biopsy, etc. Stimulation, for example, is performed by using laser energy to create zones or pockets, optionally interconnected at least initially by small channels ablated through the tissue, for the introduction of blood born growth and healing factors and stimulated capillary growth surrounding the lased zones or pockets to create an increased supply of oxygen to the tissue and thus a revitalization of the heart muscle. Methods and apparatus for causing stimulation are more fully described in co-pending U.S. patent applications Ser. No. 08/664,956 filed Jun. 13, 1996 and Ser. No. 09/182,401, which are hereby incorporated by reference.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true spirit and scope of the invention.

We claim:

1. A method of performing non-synchronous laser-assisted revascularization of myocardium, comprising the steps of:
   a) positioning a distal end of a laser energy delivery device coupled to a pulsed laser energy source having pre-selected laser parameters to avoid cardiac arrhythmia at heart tissue;
   b) allowing the distal end of the laser energy delivery device to remain stationary while emitting laser energy in at least a first and a second pulse wherein the power level increases with each pulse.

2. The method of claim 1 wherein the pulsed laser energy source is a Holmium:YAG, excimer, Nd:YAG, or Er:YAG laser.

3. The method of claim 1 wherein the pulsed laser energy source is a Holmium:YAG laser.

4. The method of claim 1 step b) wherein the increase in energy level with each pulse is 0.3 joule.

5. The method of claim 1 step b) wherein the increase in energy level with each pulse is a variable percentage in the range of about 15% to about 75%.

6. The method of claim 1 step b) wherein the increase in energy level with each pulse is a variable amount in the range of about 0.1 to 0.5 joules.

7. The method of claim 6 wherein the increase in energy level with each pulse is 40 percent.

8. The method of claim 1 step b) wherein the increase in energy level with each pulse is a fixed amount in the range of about 0.1 to 0.5 joules.

9. The method of claim 4 wherein the energy level of the first pulse is 0.7 joules and the increase in energy per pulse is a fixed amount of about 0.3 joules.

10. The method of claim 1 step b) wherein the increase in energy level with each pulse is a fixed percentage in the range of about 15% to about 75%.

11. The method of claim 10 wherein the energy level of the first pulse is 0.7 joules and the increase in energy level per pulse is 40 percent.

12. The method of claim 1 wherein the laser energy device is in combination with a surgical apparatus and step a) includes introducing the laser energy delivery device to the myocardium through the epicardium.

13. The method of claim 12 step b) wherein laser energy is emitted in seven to twenty pulses wherein the energy level increases with each pulse.

14. The method of claim 1 wherein the laser energy delivery device is in combination with a catheter apparatus and step a) includes introducing the laser energy delivery percutaneously into the vasculature and through the endocardium for positioning in the myocardium.

15. The method of claim 14 step b) wherein laser energy is emitted in two to five pulses wherein the energy level increases with each pulse.

16. The method of claim 14 step b) wherein laser energy is emitted in three pulses wherein the energy level increases with each pulse.

17. A method of performing non-synchronous laser-assisted revascularization of myocardium, comprising the steps of:
   a) determining the wavelength, energy flux, pulse width, number of pulses and energy level per pulse of the laser energy to avoid cardiac arrhythmia;
   b) positioning a distal end of a laser energy delivery device coupled to a pulsed laser energy source within myocardium;

c) allowing the distal end of the laser energy delivery device to remain stationary while emitting laser energy in at least a first and a second pulse wherein the energy level increases with each pulse.

18. The method of claim 17 wherein the pulsed laser source is a Holmium:YAG laser.

19. The method of claim 17 step b) wherein the increase in energy level with each pulse is an amount in the range of about 0.1 to 0.5 joules.

20. The method of claim 19 step b) wherein the increase in energy level with each pulse is 0.3 joules.

21. The method of claim 17 step b) wherein the increase in energy level with each pulse is a percentage in the range of about 15% to about 75%.

22. The method of claim 21 wherein the increase in energy level with each pulse is 40 percent.

23. The method of claim 17 wherein the laser energy device is in combination with a surgical apparatus and step b) includes introducing the laser energy delivery device to the myocardium through the epicardium.

24. The method of claim 23 step b) wherein laser energy is emitted in seven to twenty pulses wherein the energy level increases with each pulse.

25. The method of claim 17 wherein the laser energy delivery device is in combination with a catheter apparatus and step b) includes introducing the laser energy delivery device percutaneously into the vasculature and through the endocardium for positioning in the myocardium.

26. The method of claim 25 step b) wherein laser energy is emitted in two to five pulses wherein the energy level increases with each pulse.

27. The method of claim 25 step b) wherein laser energy is emitted in three pulses wherein the energy level increases with each pulse.

28. A method of performing non-synchronous laser-assisted revascularization of myocardium, comprising the steps of:
  a) determining the wavelength, energy flux, pulse width, number of pulses and energy level per pulse of the laser energy to avoid cardiac arrhythmia;
  b) positioning a distal end of a laser energy delivery device coupled to a pulsed laser energy source at a heart surface;
  c) allowing the distal end of the laser energy delivery device to remain stationary while emitting laser energy in at least a first and a second pulse wherein the energy level increases with each pulse.

29. The method of claim 28 wherein the pulsed laser source is a Holmium:YAG laser.

30. The method of claim 28 wherein the laser energy delivery device is in combination with a catheter apparatus and step b) includes introducing the laser energy delivery device percutaneously into the vasculature for positioning at the endocardium.

31. The method of claim 30 step b) wherein laser energy is emitted in two to five pulses wherein the energy level increases with each pulse.

32. The method of claim 30 step b) wherein laser energy is emitted in three pulses wherein the energy level increases with each pulse.

33. The method of claim 28 step b) wherein the increase in energy level with each pulse is an amount in the range of about 0.1 to 0.5 joules.

34. The method of claim 33 step b) wherein the increase in energy level with each pulse is 0.3 joules.

35. The method of claim 28 step b) wherein the increase in energy level with each pulse is a percentage in the range of about 15% to about 75%.

36. The method of claim 35 wherein the increase in energy level with each pulse is 40 percent.

37. The method of claim 28 wherein the laser energy device is in combination with a surgical apparatus and step b) includes positioning the laser energy delivery device at the epicardium.

38. The method of claim 32 step b) wherein laser energy is emitted in seven to twenty pulses wherein the energy level increases with each pulse.

* * * * *